(12) United States Patent
Kefer et al.

(10) Patent No.: US 10,488,346 B2
(45) Date of Patent: Nov. 26, 2019

(54) OBJECT MULTI-PERSPECTIVE INSPECTION APPARATUS AND METHOD THEREFOR

(71) Applicant: ABB Schweiz AG, Baden (CH)

(72) Inventors: Martin Kefer, Shanghai (CN); Jiafan Zhang, Shanghai (CN)

(73) Assignee: ABB Schweiz AG, Baden (CH)

(*) Notice: Subject to any disclaimer, the term of this patent is extended or adjusted under 35 U.S.C. 154(b) by 0 days.

(21) Appl. No.: 15/905,135

(22) Filed: Feb. 26, 2018

(65) Prior Publication Data

US 2018/0188184 A1    Jul. 5, 2018

Related U.S. Application Data

(63) Continuation of application No. PCT/CN2015/088080, filed on Aug. 26, 2015.

(51) Int. Cl.
   *G01N 21/88*    (2006.01)

(52) U.S. Cl.
   CPC ..... *G01N 21/8806* (2013.01); *G01N 21/8803* (2013.01); *G01N 2021/8841* (2013.01);
   (Continued)

(58) Field of Classification Search
   CPC ............... G01N 21/88; G01N 21/8803; G01N 21/8806; G01N 21/93; G01N 21/95;
   (Continued)

(56) References Cited

U.S. PATENT DOCUMENTS

| | | | | |
|---|---|---|---|---|
| 4,309,094 A | * | 1/1982 | Bollen | G03B 15/06 396/332 |
| 4,583,854 A | * | 4/1986 | Lozar | G01B 11/022 250/224 |

(Continued)

FOREIGN PATENT DOCUMENTS

| | | | | |
|---|---|---|---|---|
| CN | 204202647 U | | 3/2015 | |
| JP | 02183106 A | * | 7/1990 | ........... G01N 21/909 |

(Continued)

OTHER PUBLICATIONS

State Intellectual Property Office of the P.R. China, International Search Report & Written Opinion issued in corresponding Application No. PCT/CN2015/088080, dated May 30, 2016, 10 pp.

(Continued)

*Primary Examiner* — Gordon J Stock, Jr.
(74) *Attorney, Agent, or Firm* — J. Bruce Schelkopf; Taft Stettinius & Hollister LLP

(57) ABSTRACT

It is therefore an objective to provide an object multi-perspective inspection apparatus and a method therefor. The apparatus includes an image capture device; an inspection site and at least two reflection devices, being arranged for reflecting simultaneously to the image capture device at least two different side views of the object located in the inspection site; wherein: the image capture device has a field of view including the at least two different side views of the reflection. By introducing reflection devices into the inspection apparatus to enable the image capture device to "see" the part from multiple views at once, multiple surfaces can be inspected at once, in one image frame, without having the need to reposition the reflection device, the camera and/or the object for every single surface. There are more than one reflection devices placed in the camera's field of view to assist the inspection process by exploiting otherwise hidden surfaces of any given solid object. The effort inspecting (Continued)

every single part form multiple sides is reduced. Therefore, the period of the inspection cycle time can be reduced and inspection on the level of multi-surfaces becomes possible increasing overall quality.

10 Claims, 3 Drawing Sheets

(52) U.S. Cl.
CPC ............. *G01N 2201/0636* (2013.01); *G01N 2201/0638* (2013.01)

(58) Field of Classification Search
CPC ........... G01N 21/9501; G01N 21/9503; G01N 21/9506; G01N 21/9508; G01N 21/951; G01N 21/9515; G01N 21/956; G01N 21/95607; G01N 21/95684; G01N 21/95692; G01N 21/958; G01N 2021/887; G01N 2021/8887; G01N 2021/889; G01N 2021/8893; G01N 2021/95615; G01N 2021/95638; G01N 2021/95646; G01N 2021/95653; G01N 2021/95661; G01N 2021/956669; G01N 2021/95676; G01N 2201/0636; G01N 2201/0638
USPC .............. 356/600, 388, 390, 394, 445, 448, 356/237.1–237.6, 238.1–238.3, 356/239.1–239.8, 240.1; 382/141–150, 382/152
See application file for complete search history.

(56) References Cited

U.S. PATENT DOCUMENTS

| | | | |
|---|---|---|---|
| 4,601,577 A | 7/1986 | Gotou et al. | |
| 4,731,649 A * | 3/1988 | Chang | G01N 21/9054 250/223 B |
| 4,959,898 A * | 10/1990 | Landman | H05K 13/08 29/705 |
| 5,126,872 A * | 6/1992 | Birkle | G01N 21/952 356/24 |
| 5,173,796 A * | 12/1992 | Palm | G01B 11/02 250/234 |
| 5,420,689 A * | 5/1995 | Siu | G01N 21/956 356/394 |
| 5,452,080 A * | 9/1995 | Tomiya | G01N 21/88 356/237.1 |
| 5,519,496 A * | 5/1996 | Borgert | G01N 21/8806 348/126 |
| 5,528,371 A * | 6/1996 | Sato | G01N 21/88 348/126 |
| 5,563,703 A * | 10/1996 | Lebeau | H05K 13/08 348/126 |
| 5,864,405 A * | 1/1999 | Ikeno | H05K 13/08 356/390 |
| 5,909,285 A * | 6/1999 | Beaty | G01N 21/88 356/394 |
| 5,910,844 A * | 6/1999 | Phillips | G01N 21/88 356/614 |
| 5,917,655 A * | 6/1999 | Lehnen | G02B 5/04 348/E13.005 |
| 6,055,054 A * | 4/2000 | Beaty | G01N 21/88 356/601 |
| 6,055,055 A * | 4/2000 | Toh | G01N 21/88 250/559.46 |
| 6,088,108 A * | 7/2000 | Toh | G01N 21/95684 356/614 |
| 6,128,034 A * | 10/2000 | Harris | H05K 13/08 348/126 |
| 6,242,756 B1 * | 6/2001 | Toh | G01N 21/95684 250/559.34 |
| 6,307,210 B1 * | 10/2001 | Suzuki | G01N 21/88 250/559.08 |
| 6,359,694 B1 * | 3/2002 | Stredele | G01N 21/8806 356/237.1 |
| 6,445,518 B1 * | 9/2002 | Lee | H05K 13/0812 359/833 |
| 6,532,063 B1 * | 3/2003 | Tan | G01N 21/95684 356/237.1 |
| 6,573,987 B2 * | 6/2003 | Shires | G01N 21/95684 348/126 |
| 6,813,016 B2 * | 11/2004 | Quist | G01N 21/8806 250/559.08 |
| 7,019,771 B1 * | 3/2006 | Bollinger | H05K 13/0812 348/125 |
| 7,283,235 B2 * | 10/2007 | Salvi | G01N 21/95684 250/559.08 |
| 7,423,743 B2 * | 9/2008 | Smets | H05K 13/08 356/237.1 |
| 7,477,374 B2 * | 1/2009 | Schmidt | B07C 5/3408 250/223 B |
| 7,570,359 B2 * | 8/2009 | Fox | A61B 5/0071 356/417 |
| 9,816,938 B2 * | 11/2017 | Amanullah | H04N 5/2256 |
| 2007/0279622 A1 | 12/2007 | Yamauchi et al. | |
| 2008/0239301 A1 | 10/2008 | Yokota et al. | |
| 2009/0002694 A1 | 1/2009 | Paavola | |
| 2009/0173725 A1 | 7/2009 | Holcomb et al. | |
| 2014/0240488 A1 | 8/2014 | Kanou | |
| 2015/0002653 A1 | 1/2015 | Hwang et al. | |

FOREIGN PATENT DOCUMENTS

| | | | |
|---|---|---|---|
| JP | 03137502 A * | 6/1991 | |
| JP | 05060538 A | 3/1993 | |
| JP | 06273339 A * | 9/1994 | |
| JP | H1151620 A | 2/1999 | |
| JP | 2005172608 A | 6/2005 | |
| JP | 2007114180 A | 5/2007 | |
| JP | 2007147433 A | 6/2007 | |
| TW | 201331574 A | 8/2013 | |

OTHER PUBLICATIONS

First Japanese Office Action, Japanese Patent Application No. 2018-510332, dated Jan. 8, 2019, 13 pages including English Translation.

Extended European Search Report, European Patent Application No. 15901981.9, dated Mar. 7, 2019, 7 pages.

Decision of Rejection issued in corresponding Japanese application No. 2018-510332, dated Aug. 6, 2019, 8 pp.

* cited by examiner

OBJECT MULTI-PERSPECTIVE INSPECTION APPARATUS AND METHOD THEREFOR

TECHNICAL FIELD

The invention relates to investigating and analysing object by use of optical means, and more particularly to apparatus for inspecting object from multi-perspective with optical means and method therefor.

BACKGROUND ART

Visual cosmetic inspection is commonly used for quality control, data acquisition, and data analysis. This is an important commercial function, which may be used for example, for visually distinguishing between flawed and flawless product from production/manufacturing/assembly processes of 3C industry.

A conventional approach is to analyse product samples, surface by surface, which eventually takes long time. Given a certain throughput rate of any given production process, only a small number of samples can be inspected. In other words, some defective products may be identified as flawless without inspection and reaches the end of the production line. Therefore, the operator has to make a compromise between the production rate and the product quality rate. For example, a visual cosmetic inspection apparatus is disclosed in Patent US 20080239301 A1 for performing visual inspection of an object form a multiple of perspectives, which uses observation optical system, a first mirror and two second mirrors. By rotating the first mirror while moving it integrally with the observation optical system, observation of the side surface of the object, such as a wafer. Besides, the views of a top surface and bottom surface may be obtained by moving and rotating the first mirror and the two second mirrors integrally with the observation optical system. Therefore, a period of the inspection cycle time has to be set long enough to allow the completion of the repositioning of the mirrors for a multi-perspective inspection, which decreases the inspection rate.

BRIEF SUMMARY OF THE INVENTION

It is therefore an objective of the invention to provide an object multi-perspective inspection apparatus, including: an image capture device; an inspection site and at least two reflection devices, being arranged for reflecting simultaneously to the image capture device at least two different side views of the object located in the inspection site; wherein: the image capture device has a field of view including the at least two different side views of the reflection.

According to another aspect of present invention, it provides a method of object inspection, including: reflecting at least two different side views of the object simultaneously; capturing images of the at least two different side views of the reflection; and comparing the captured images of the views of an object without defect and those of the object under inspection.

By introducing reflection devices into the inspection apparatus to enable the image capture device to "see" the part from multiple views at once, multiple surfaces can be inspected at once, in one image frame, without having the need to reposition the reflection device, the camera and/or the object for every single surface. There are more than one reflection devices placed in the camera's field of view to assist the inspection process by exploiting otherwise hidden surfaces of any given solid object. The effort inspecting every single part from multiple sides is reduced. Therefore, the period of the inspection cycle time can be reduced and inspection on the level of multi-surfaces becomes possible increasing overall quality.

Preferably, the at least two reflection devices are arranged to guide the lights directly from the object; and each of the two reflection devices is inclined by a predetermined a—ngle with respect to an optical axis of the image capture device so that the image capture device receives the reflected side view of the object directly therefrom. Such arrangement of the observation angle makes it possible to place the reflection devices in direct line of sight of the image capture device. Therefore, it provide an economic solution without deploying extra reflection devices.

Preferably, the at least two reflection devices are arranged for reflecting simultaneously to the image capture device top view of the object located in the inspection site so that the image capture device receives the reflected top view of the object directly therefrom. Therefore, the field of view of the reflection device may be enlarged to cover the top view of object and he controller may conduct the comparison concerning the part relevant to the top view of the object appearing in the images for the top view and the side views. This is advantageous since light falling onto a surface from one side can only reveal a certain set of defects. Provided throughout the mirrors, light does not only fall onto the surface in one direction, but in at least one more angle. These different views of one and the same surface can be seen in the mirrors, leading to a more thorough investigation in only one image frame. In addition, in the image frame the static scene can easily be masked, so that only the areas of interest are analyzed.

Preferably, lengths of optical paths of the lights are substantially the same to ensure an equal degree of focus for images captured from the views of the object reflected by the at least one reflection devices.

Preferably, the object multi-perspective inspection apparatus further includes: a refracting device having a first surface for supporting the object located in the inspection site and a second surface having an angle deviating from the first surface, being arranged to refracting a bottom view of the object in the inspection site to a first of the at least two reflection devices; wherein the first reflection device receives the refracted bottom view of the object and reflects the received to the image capture device. Since the refracting device is reused for both of mechanical support of the object and deflecting its bottom view to one of the reflection devices, the cost can be reduced for the multi-perspective inspection apparatus and compatibility thereof can be increased. Besides, one of the reflection devices is reused for reflecting the object bottom view to the image capture device in addition to the side view and/or the top view of the object, which further reduces the cost and increases the compatibility of the object multi-perspective inspection apparatus.

Preferably, the object multi-perspective inspection apparatus further includes a processor, being adapted for comparing captured images of the views of an object without defect and those of the object under inspection. Since the template images and the images concerning the object to be inspected both are affected by the same level of distortion, the negative influence of the distortion can be compromised and thus the identification result is accurate. Surface analysis can be done either using template-based or machine-learning based algorithm. Calibration of any kind is not needed since, in any case, differences from good parts are investigated.

Images from good parts, which would serve as templates or as a basis for learning procedures, would be acquired using the exact same setup as later on in the actual inspection process.

BRIEF DESCRIPTION OF THE DRAWINGS

The subject matter of the invention will be explained in more detail in the following text with reference to preferred exemplary embodiments which are illustrated in the drawings, in which.

The reference symbols used in the drawings, and their meanings, are listed in summary form in the list of reference symbols. In principle, identical parts are provided with the same reference symbols in the figures.

PREFERRED EMBODIMENTS OF THE INVENTION

In the following description, for purposes of explanation and not limitation, specific details are set forth, such as particular circuits, circuit components, interfaces, techniques, etc. in order to provide a thorough understanding of the present invention. However, it will be apparent to one skilled in the art that the present invention may be practiced in other embodiments that depart from these specific details. In other instances, detailed descriptions of well-known methods and programming procedures, devices, and circuits are omitted so not to obscure the description of the present invention with unnecessary detail.

Figure 1A:
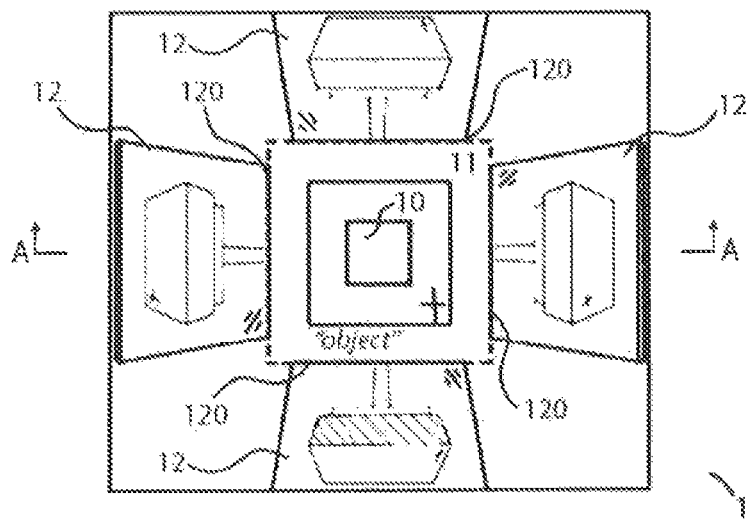
FIGS. 1A and 1B respectively show an object multi-perspective inspection apparatus according to an embodiment of present invention and its sectional drawing taken along line A-A of FIG. 1A.
Figure 1B:
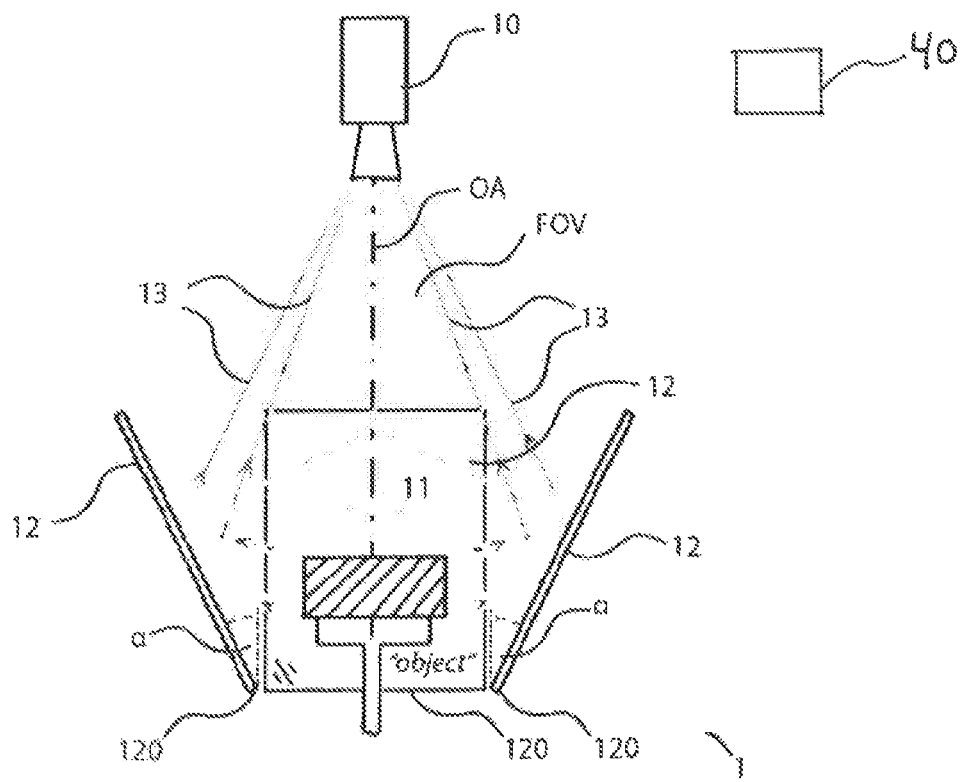

FIGS. 1A and 1B respectively show an object multi-perspective inspection apparatus according to an embodiment of present invention and its sectional drawing taken along line A-A of FIG. 1A. As shown in FIGS. 1A and 1B, the object multi-perspective inspection apparatus 1 includes an image capture device 10, an inspection site 11 and at least two reflection devices 12. The image capture device 10 may be a camera to receive the light from the object to be inspected, either reflected or refracted through various optical paths (the camera can be in communication with a processor 40 for comparing captured images). The image capture device 10 therefore has a field of view FOV covering a part of the world that is visible through the image capture device 10, while views of articles outside of the field of view FOV is not. The reflection device 12 may be a mirror to guide light from the object to the image capture device 10. The mirror may be selected as plane mirror, concave mirror or convex mirror. Preferably, the reflection device 12 uses plane mirror. A parallel beam of light changes its direction as a whole, while still remaining parallel; the images formed by a plane mirror are virtual images, of the same size as the original object.

Depending on the requirement of how many side views of the object to be inspected, the number of reflection device may be selected from two to four, so long as it counts more than one for the sake of multi-perspective observation. In this embodiment according to FIGS. 1A and 1B, at least two reflection devices 12 are used to reflect simultaneously to the image capture device 10 the at least two different side views of the object located in the inspection site 11. For example, the four side views of the object are simultaneously provided to the camera 10 for using the four mirrors 12 with optical paths 13 corresponding to the four side views. The image capture device 10 has a field of view FOV including the at least two different side views of the reflection. In this example, images of the four side views of the object are captured by the camera 10 as the side views are reflected by the mirrors 12 and pass through the inspection site 11, and they would not overlap with each other in the sight of the camera 10 since the field of view of the camera 10, as above mentioned, covers the side views of the reflection, where the optical paths 13 reflected from the four mirrors 12 corresponding to the four side views of the object extend and reach the camera 10. This makes it possible, from a perspective of the camera, distinguish between the contours of different images corresponding to the different side views.

By introducing reflection devices into the inspection apparatus to enable the camera to "see" the part from multiple views at once, multiple surfaces can be inspected at once, in one image frame, without having the need to reposition the reflection device, the camera and/or the object for every single surface. There are more than one reflection devices placed in the camera's field of view to assist the inspection process by exploiting otherwise hidden surfaces of any given solid object. The effort inspecting every single part from multiple sides is reduced. Therefore, the period of the inspection cycle time can be reduced while ensuring high quality throughout simultaneous multi-surface inspection.

As shown in FIG. 1B, preferably the at least two reflection devices 12 are arranged to guide the lights directly from the object, and each of the two reflection devices 12 is inclined by a predetermined inclination angle α with respect to an optical axis OA of the image capture device 10 so that the reflection surface of the reflection device 12 may be positioned facing the image capture device 10 and thus the field of view FOV the image capture device 10 may have a workable coverage and the image capture device 10 can receive the reflected side view of the object directly from the reflection device 12. For example, where the plane of the mirror 12 may be positioned to be inclined outwards by 30 degrees with respective to the optical axis of the camera 10, the side views of the object can be observed by the camera 10 with the optical paths 13 passing through the inspection site 11. Such arrangement of the observation angle makes it possible to place the reflection devices in direct line of sight of the image capture device. Therefore, it provide an economic solution without deploying extra reflection devices. For example, this approach is cost-effective, since only one camera with a few reflecting devices is required for multiple view analysis, compared to multiple cameras.

In addition, the reflection devices 12 may be arranged such that the lengths of optical paths 13 of the lights are substantially the same to ensure an equal degree of focus for images captured from the at least two different side views of the object of the reflection. For example, as shown in FIGS.

1A and 1B, each of the four mirrors 12 may be placed where one of its sides aligned with a side of the bottom surface of the inspection site 11 as indicated by reference sign 120 and have the inclination angle α with the bottom surface of the inspection site 11.

As described in the foregoing part, the object multi-perspective inspection apparatus 1 can observe more than one side views of the object at once, leaving the top view unattended. In order to inspect the top surface of the object at the same time, the at least two reflection devices 12 may be arranged around the inspecting site 11, and the field of view FOV of the image capture device 10 may further include top view of the object located in the inspection site. For example, as shown in FIG. 1B, where the mirrors 12 are placed to surround the inspection site 11 with the inclination angle α enabling its reflection surface facing the camera 10, there is no article obstructing the optical path starting from a top surface of the object and the camera 10. Besides, because the field of view FOV of the camera 10 has a workable coverage of the mirrors 12 surrounding the inspection site 11 where the object should be placed, it must cover the top view of the object as well. Again due to such workable field of view FOV of the image capture device 10, the images acquired from the top view and the side views of the object are distinguishable from each other. By capturing the image of the top view of the object which otherwise would not be obtained in the apparatus for inspection of side views, the workable field of view FOV of the image capture device can be utilized to its full extent for the multi-perspective inspection simultaneous. Therefore, there is no need for an additional camera for imaging the top view or a mechanism for repositioning the camera to direct its sight to the top view of the object.

Figure 2A:
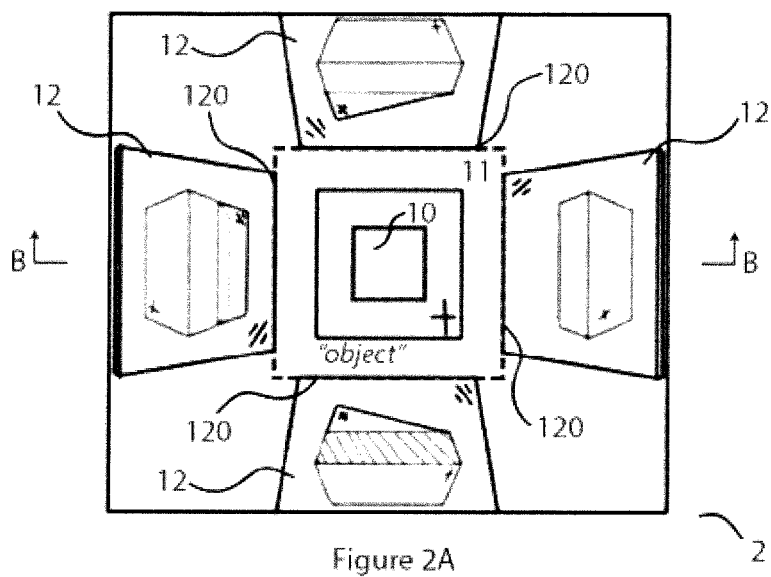
FIGS. 2A and 2B respectively show an object multi-perspective inspection apparatus according to another embodiment of present invention and its section drawing taken along line B-B of FIG. 2A.
Figure 2B:
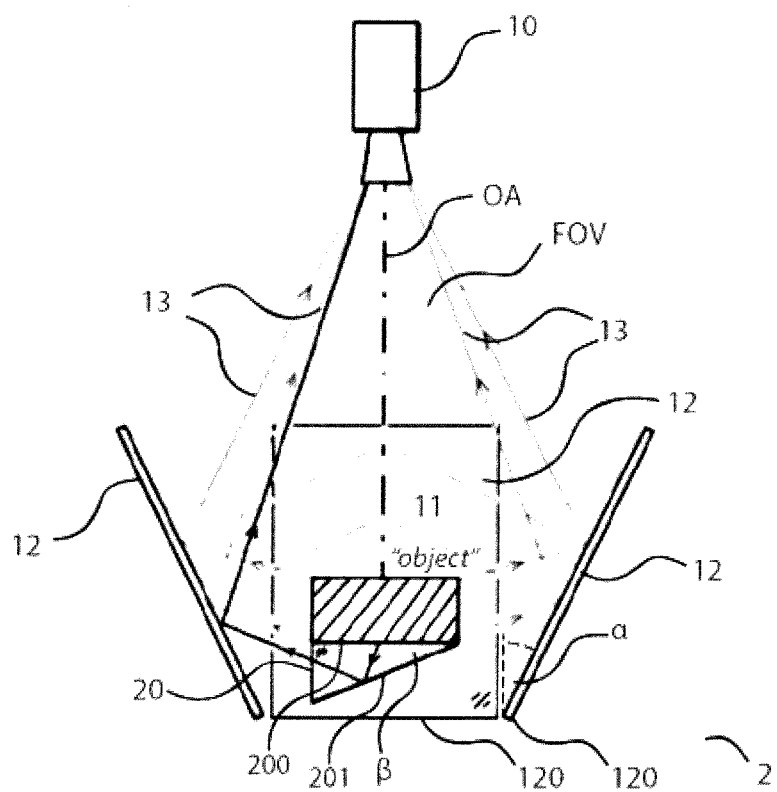

FIGS. 2A and 2B respectively show an object multi-perspective inspection apparatus according to another embodiment of present invention and its section drawing taken along line B-B of FIG. 2A. The embodiments according to FIGS. 2A and 2B are substantially similar to that according to FIGS. 1A and 1B, except in that the former further includes a refracting device 20. For avoidance of redundancy, the description concerning their common parts are omitted here. The same reference signs indicate the same part. As shown in FIGS. 2A and 2B, the object multi-perspective inspection apparatus 2 has the refracting device 20 with functionality of support of the object. The refracting device 20 has a first surface 200 for supporting the object located in the inspection site 11 and a second surface 201 having an deflection angle β deviating from the first surface 200, being arranged to refracting a bottom view of the object in the inspection site 11 to a first of the at least two reflection devices 12. For example, the refracting device 20 may be a deflecting prism made of transparent materials having a predetermined mechanical strength, such as glass, plastic and fluorite. The deflecting prism 20 is fixed in the inspection site 11, where its first surface 200 may mechanically support the bottom surface of the object in the inspection site 11, and thus object can be mounted on the first surface 200 of the deflecting prism 20. The deflection angle β between the first surface 200 and the second surface 201 may be predetermined so that a light beam from the bottom surface of the object can enter the deflecting prism 20 and then be deflected by the second surface 201 to one of the mirrors 12, for example the mirror 12 to the left of the inspection site 11 (the first reflection device). The first reflection device 12 may receive the refracted bottom view of the object and reflect the received to the image capture device 10. In such arrangement, the refracting device provides an integrated functionalities including supporting the object and directing its bottom view to the image capture device for the multi-perspective inspection simultaneous.

Preferably, the deflection angle β between the first surface 200 and the second surface 201 of the refracting device 20 is arranged so that a field of view of the first reflection device includes the side view and bottom view of the object of the refraction. It is physically impossible that the side view and bottom overlap in the image, because the edge of the object between these two views is preventing light reflecting from the bottom of the object to fall on the virtual image of the side view in the reflection device. Since one of the reflection devices is reused for reflecting the object bottom view to the image capture device, the cost can be reduced for the multi-perspective inspection apparatus according to present invention. A controller may be used for flaw identification (not shown in the figures). It can be used for comparing captured images of the views of an object without defect and those of the object under inspection. The reflection of side views and/or bottom view of the object may introduce distortion of the images as obtained by the image capture device 10 because of the inclination angle α of the reflection device with respect to the optical axis of the image capture device and the deflection angle β between the first surface and the second surface of the refraction device. The controller may instruct the image capture device 10 to obtain images of the different views of a flawless object as a template and store them as template in a memory. The controller may further compare the template with the images of the views of an object to be inspected so as to judge if the latter is flawed or not. Since the template images and the images concerning the object to be inspected both are affected by the same level of distortion, the negative influence of the distortion can be compromised and thus the identification result is accurate. Surface analysis can be done either using template-based or machine-learning based algorithm. Calibration of any kind is not needed since, in any case, differences from good parts are investigated. Images from good parts, which would serve as templates or as a basis for learning procedures, would be acquired using the exact same setup as later on in the actual inspection process.

Figure 3A:
FIGS. 3A, 3B, 3C and 3D respectively show a side view of the object as the template, an image of the side view of the object as template as obtained by the image acquire device, an image of side view of a flawless object under inspection as obtained by the image acquire device and that of a flaw object.
Figure 3B:
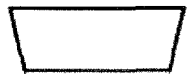
Figure 3C:
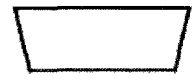
Figure 3D:
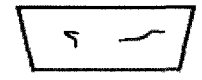

For example, FIGS. 3A, 3B, 3C and 3D respectively show a side view of the object as the template, an image of the side view of the object as template as obtained by the image acquire device, an image of side view of a flawless object under inspection as obtained by the image acquire device and that of a flaw object. As shown in FIG. 3A, a contour of the side view of the template is rectangle-shaped. In contrast due to the influence of the distortion, the contours for image of the template of FIG. 3B, the image of the flawless object side view of FIG. 3C and the image of the flawed object side view of FIG. 3D all look like trapezoid. Some defects, such as the dots and scratches, appear in the image of the flawed according to FIG. 3D, while the images for the template and the flawless as shown in FIGS. 3B and 3C do not present the defects which are more similar to each other. Therefore, the controller can determine if an object under inspection has defects or not by using template-based algorithm, in spite of the influence of distortion induced by the reflection of the side view. The skilled person in the art should understand that the template-based algorithm may be applied to defect detection for the bottom of the object because its bottom view may be reflected to the image capture device according to the solution as described above.

Figure 4A:
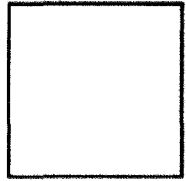
FIGS. 4A, 4B and 4C respectively show an image of the top view of the object as template as obtained by the image acquire device, an image of top view of a flawless object under inspection as obtained by the image acquire device and that of a flaw object.
Figure 4B:
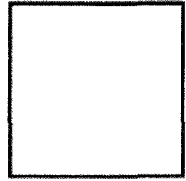
Figure 4C:

FIGS. 4A, 4B and 4C respectively show an image of the top view of the object as template as obtained by the image acquire device, an image of top view of a flawless object under inspection as obtained by the image acquire device and that of a flaw object. No perspective distortion is introduced to the images according to FIGS. 4A, 4B and 4C because the image capture device is placed facing the top view of the object. As shown in FIGS. 4A, 4B and 4C, the contours for the image of the top view of the template, the image of the flawless top view and the image of the flawed top view all are rectangle-shaped. Some defects, such as the dots and scratches, appear in the image of the flawed according to FIG. 4C, while the images for the template and the flawless as shown in FIGS. 4A and 4B do not present the defects which are more similar to each other. Therefore, the controller can determine if an object under inspection has defects or not by using template-based algorithm.

Alternatively, the at least two reflection devices 12 may be arranged for reflecting simultaneously to the image capture device 10 top view of the object located in the inspection site so that the image capture device 10 may receive the reflected top view of the object directly therefrom. Therefore, the field of view of the reflection device may be virtually enlarged to cover the top view of object. For example, as shown in FIGS. 1A and 1B, the top surface marked with a cross in the corner can be seen in the images for the top view and the side views to the image capture device 10. The controller may conduct the comparison concerning the part relevant to the top view of the object appearing in the images for the top view and the side views. This is advantageous since light falling onto a surface from one side can only reveal a certain set of defects. Provided throughout the mirrors, light does not only fall onto the surface in one direction, but in at least one more angle. These different views of one and the same surface can be seen in the mirrors, leading to a more thorough investigation in only one image frame. In addition, in the image frame the static scene can easily be masked, so that only the areas of interest are analyzed. In addition, the reflection devices 12 may be arranged such that the lengths of optical paths 13 of the lights are substantially the same to ensure an equal degree of focus for images captured from the at top view of the object of the reflection.

Though the present invention has been described on the basis of some preferred embodiments, those skilled in the art should appreciate that those embodiments should by no way limit the scope of the present invention. Without departing from the spirit and concept of the present invention, any variations and modifications to the embodiments should be within the apprehension of those with ordinary knowledge and skills in the art, and therefore fall in the scope of the present invention which is defined by the accompanied claims.

The invention claimed is:

1. An object multi-perspective inspection apparatus, including:
   an image capture device;
   an inspection site;
   at least two reflection devices, being arranged for reflecting simultaneously to the image capture device at least two different side views of the object located in the inspection site; and
   a refracting device having a first surface for supporting the object located in the inspection site and a second surface having an angle deviating from the first surface, being arranged to refract a bottom view of the object in the inspection site to a first of the at least two reflection devices;
   wherein:
   the image capture device has a field of view including the at least two different side views of the reflection; and
   a first of the at least two reflection devices receives the refracted bottom view of the object and reflects the received refracted bottom view of the object to the image capture device.

2. The object multi-perspective inspection apparatus according to claim 1, wherein:
   the at least two reflection devices are arranged around the inspecting site; and
   the field of view of the image capture device further includes top view of the object located in the inspection site.

3. The object multi-perspective inspection apparatus according to claim 1, wherein:
   the angle between the first surface and the second surface of the refracting device is arranged so that a field of view of the first reflection device includes the side view and refracted bottom view of the object.

4. The object multi-perspective inspection apparatus according to claim 1, further including:
   a processor, being adapted for comparing captured images of views of an object without defect and those of the object under inspection.

5. The object multi-perspective inspection apparatus according to claim 1, wherein:
   the at least two reflection devices are arranged to guide light directly from the object; and
   each of the at least two reflection devices is inclined by a predetermined angle with respect to an optical axis of the image capture device so that the image capture device receives the reflected side view of the object directly therefrom.

6. The object multi-perspective inspection apparatus according to claim 5, wherein:
   lengths of optical paths of the light are substantially the same to ensure an equal degree of focus for images captured from the views of the reflection.

7. The object multi-perspective inspection apparatus according to claim 5, wherein:
   the at least two reflection devices are arranged around the inspecting site; and
   the field of view of the image capture device further includes top view of the object located in the inspection site.

8. The object multi-perspective inspection apparatus according to claim 5, further including:
   a processor, being adapted for comparing captured images of views of an object without defect and those of the object under inspection.

9. The object multi-perspective inspection apparatus according to claim 5, wherein:
   the at least two reflection devices are arranged for reflecting simultaneously to the image capture device top view of the object located in the inspection site so that the image capture device receives the reflected top view of the object directly therefrom.

10. The object multi-perspective inspection apparatus according to claim 9, wherein:
    lengths of optical paths of the light are substantially the same to ensure an equal degree of focus for images captured from the views of the reflection.

* * * * *